United States Patent [19]

Dell'Orto et al.

[11] Patent Number: 4,793,189
[45] Date of Patent: Dec. 27, 1988

[54] THICK-FILM STRAIN GAUGE FOR SENSING STRESSES & STRAINS IN MECHANICAL MEMBERS OR STRUCTURES

[75] Inventors: Giuseppe Dell'Orto, Milan; Giuseppina Rossi, Pavia, both of Italy

[73] Assignee: Marelli Autronica S.p.A., Pavia, Italy

[21] Appl. No.: 115,557

[22] Filed: Nov. 2, 1987

Related U.S. Application Data

[63] Continuation of Ser. No. 908,467, Sep. 17, 1986, abandoned.

[30] Foreign Application Priority Data

Sep. 17, 1985 [IT] Italy .............................. 53804/85[U]

[51] Int. Cl.[4] .............................................. G01B 7/20
[52] U.S. Cl. ...................................................... 73/775
[58] Field of Search ................. 73/774, 775, 781, 782, 73/862.35, 777, 862.48, 763, 768, 855, 862.04, 862.06; 338/5, 47, 2, 6, 3, 4, 36

[56] References Cited

U.S. PATENT DOCUMENTS

| | | | |
|---|---|---|---|
| 2,599,578 | 6/1952 | Obert et al. | 73/775 |
| 2,626,338 | 1/1953 | Mitchell | 73/775 |
| 2,722,587 | 11/1955 | Buzzetti et al. | 73/781 |
| 2,982,127 | 5/1961 | Scott | 73/775 |
| 3,327,270 | 6/1967 | Garrison | 338/5 |
| 3,411,348 | 11/1968 | Schultheis, Jr. | 73/775 |
| 3,479,739 | 11/1969 | Stedman | 338/6 |
| 3,695,096 | 10/1972 | Kutsay | 73/775 |
| 3,738,162 | 6/1973 | Dally et al. | 73/775 |
| 3,899,695 | 8/1975 | Solomon et al. | 73/727 |
| 4,055,078 | 10/1977 | D'Antonio et al. | 73/774 |
| 4,322,980 | 4/1962 | Suzuki et al. | 73/727 |
| 4,424,717 | 1/1984 | White | 338/5 |
| 4,481,497 | 11/1984 | Kurtz et al. | 73/721 |
| 4,553,872 | 11/1985 | Chandra et al. | 73/855 |
| 4,586,018 | 4/1986 | Bettman | 73/720 |

FOREIGN PATENT DOCUMENTS

0150816 9/1983 Japan .................................. 73/763

OTHER PUBLICATIONS

Bethe et al., "Thin-Film Strain Gauge Transducers", Philips Tech. Rev. 39, No. 3/4, 94–101, 1980.

*Primary Examiner*—Stewart J. Levy
*Assistant Examiner*—Robert R. Raevis
*Attorney, Agent, or Firm*—Sughrue, Mion, Zinn, Macpeak and Seas

[57] ABSTRACT

A strain gauge sensor for sensing stresses and deformations in mechanical members or structures, comprising a support substrate in form of a thin plate, made of an electrically-insulating material, preferably ceramic material, bearing on one face at least one thick-film resistor; said support substrate being adapted to be firmly attached with its other face onto a member or structure of which stresses and deformations are to be locally sensed, so that said stresses or deformations determine through the substrate corresponding deformations of said at least one thick-film resistor.

1 Claim, 2 Drawing Sheets

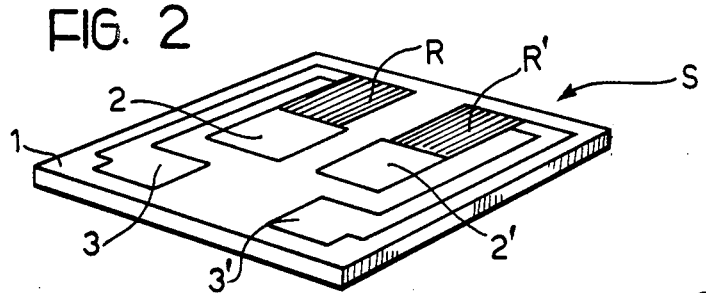
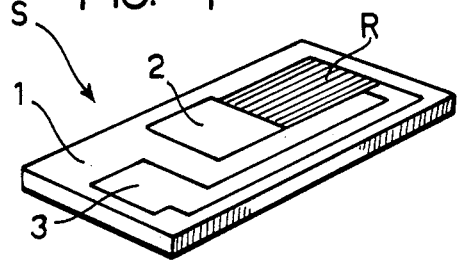
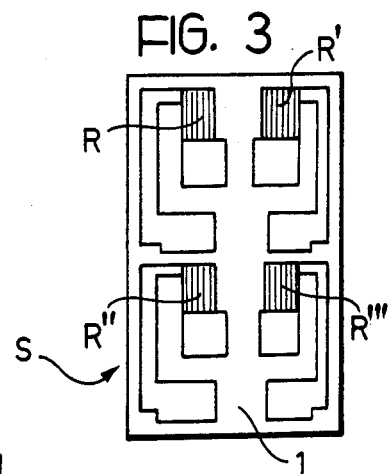
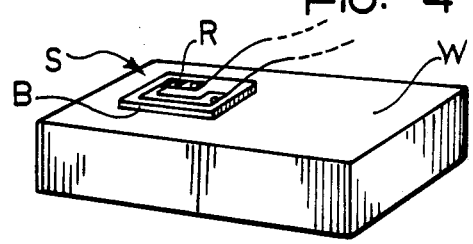
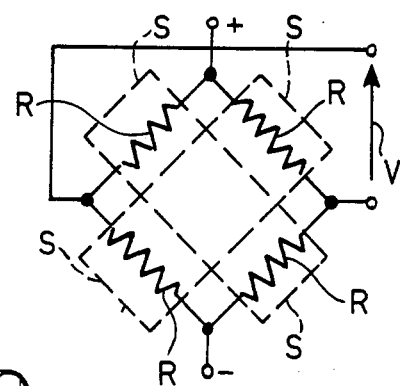
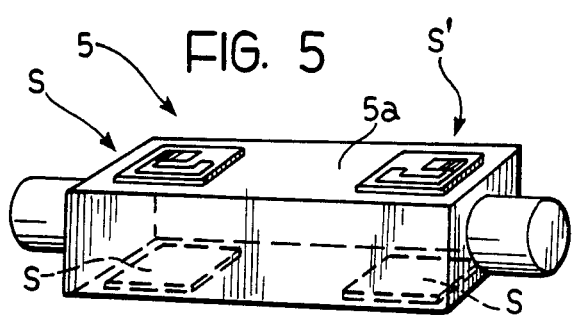

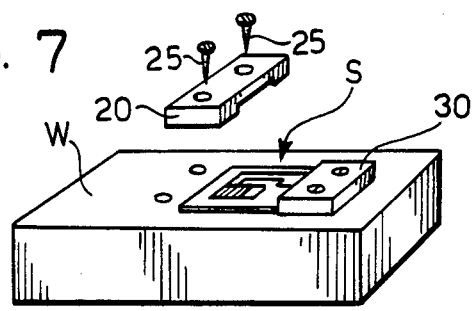
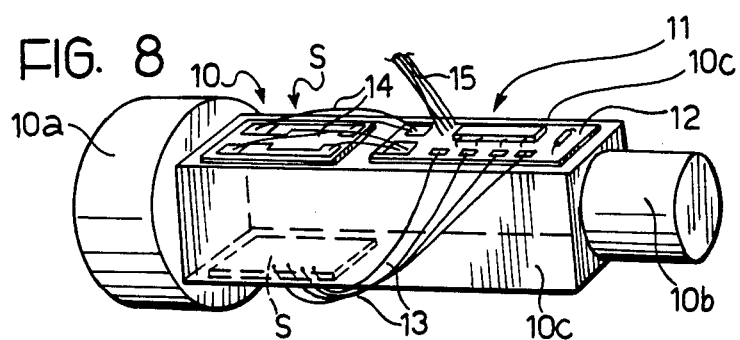
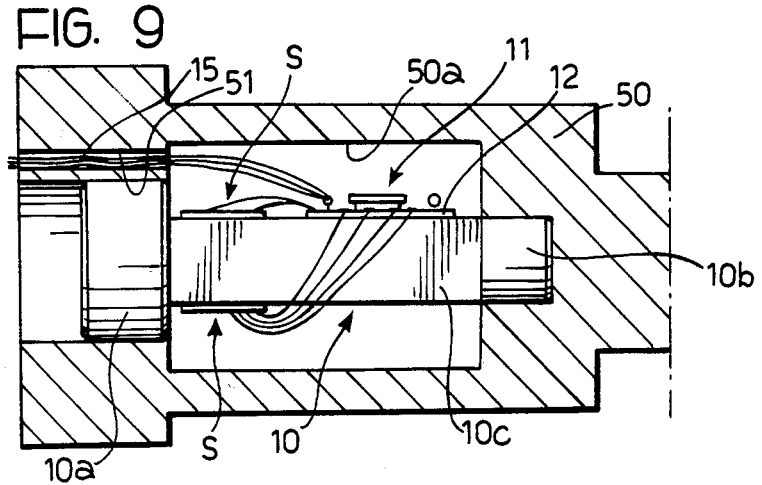
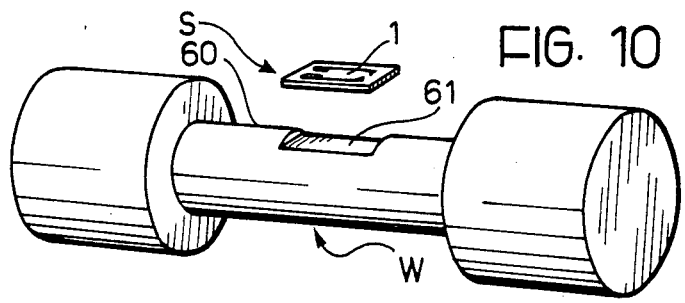

THICK-FILM STRAIN GAUGE FOR SENSING STRESSES & STRAINS IN MECHANICAL MEMBERS OR STRUCTURES

This application is a continuation of application Ser. No. 908,467, filed 9/17/86, now abandoned.

The present invention relates to a strain gauge for sensing stresses or deformations in mechanical members or structures.

The object of the present invention is to provide a strain gauge sensor which can be simply and cheaply manufactured, which is of versatile use, and having a very high sensitivity to the stresses and strains to be sensed.

This object is achieved according to the invention by means of a strain gauge sensor characterized in that it comprises a support substrate in form of a thin plate, made of an electrically-insulating material, preferably ceramic, on one face of which at least one thick-film resistor is applied; said support substrate being adapted to be firmly attached with its other face to a member or structure, the stresses or deformations of which are to be locally sensed, so that said stresses or deformations determine through the substrate corresponding deformations of said at least one thick-film resistor.

According to a further characteristic the said substrate on its said other face is provided with a layer of a gluing or cementing material.

As an alternative, the said substrate may be provided with mechanical fastening or clamping means adapted to allow its attachment to the said member or structure.

Further characteristics and advantages of the strain gauge sensor according to the present invention will become apparent from the detailed description which follows with reference to the appended drawings, provided purely by way of non-limiting example, in which:

FIG. 1 is a perspective view of a sensor according to the invention,

FIG. 2 is another perspective view of a sensor according to the invention,

FIG. 3 is a plan view of another sensor according to the invention,

FIG. 4 is a perspective view showing one way of applying a sensor according to the invention to a mechanical member, FIG. 5 is a perspective view of another mechanical member provided with four sensors according to the invention, FIG. 6 is an electric diagram which shows an example of electrical connection of the sensors applied to the member shown in FIG. 5, FIG. 7 is a perspective view which shows a different way of clamping a sensor according to the invention onto a mechanical member, FIG. 8 is a perspective view which illustrates a way of mounting two sensors according to the invention and an electronic circuit for processing the signals thereby generated, FIG. 9 is a side elevational view, partially sectioned, of a shaft in which the device shown in FIG. 8 is mounted, and FIG. 10 is a perspective view which shows a further way of mounting the sensor according to the invention.

With reference to FIG. 1, the simplest embodiment of a sensor S according to the present invention comprises a thin rectangular plate 1 of electrically-insulating material, preferably ceramics. On one face of said plate a thick-film resistor R is deposited by the known silk-screen techniques. On the same face of the plate there are applied metal tracks 2 and 3, which are connected with resistor R and which allow the electrical connection to other devices, for example other similar resistors, or external processing circuits.

In FIG. 2 a sensor is shown, on the support plate 1 of which there are applied two thick-film resistors R, R' and their respective metal connection tracks 2, 3 and 2', 3'. The resistors R, R' can have the same or different shapes as well as the same or different resistances.

FIG. 3 shows a sensor S according to the invention, in which on same support plate four thick-film resistors, R, R', R" and R'" are deposited.

As shown for example in FIG. 4, a sensor S can be applied onto a mechanical member by interposition of a layer B of a glue or cement.

FIG. 5 shows another way of using sensors according to the invention: on two opposite faces of the intermediate prismatic portion 5a of a pin 5 there are glued four sensors S according to the invention. Said sensors can be conveniently electrically connected to each other in the way shown in FIG. 6, in which R indicates the resistance of the thick-film resistors of the sensors S. To one diagonal of the bridge circuit a d.c. supply voltage is applied, and between the vertices of the other diagonal there is in use available a voltage signal V which varies as a function of the magnitude of the stresses to which pin 5 is subjected.

Another application of the sensors according to the invention is shown in FIG. 8. In this figure a metal piece indicated 10 has two cylindrical end portions 10a, 10b and an intermediate prismatic portion 10c. On two opposite faces of the intermediate prismatic portion there are applied two sensors S according to the present invention, of the kind illustrated in FIG. 2, i.e. having each a pair of thick-film resistors. Near each of said sensors, onto the intermediate portion 10c there is glued an electronic amplifier circuit indicated 11, which is mounted on an insulating plate 12 glued on the piece 10 by means of a soft glue adapted for damping vibrations. The sensors S are connected to circuit 11 by means of wires 13 and 14, while the wires through which circuit 11 is supplied and the signal thereby generated is delivered are indicated 15.

The embodiment shown in FIG. 8 makes it possible to sense torsional and flexural stresses acting on the member 10. This embodiment can be used in the way illustrated in FIG. 9, to sense the stresses acting on the shaft 50; to this end the device shown in FIG. 8 is mounted in an axial recess 50a at one end of the shaft. The cylindrical end portions of the said device can be fixed in corresponding portions having a smaller diameter of the recess of the shaft 50, by means of glues or cements or other locking means known per se, such as pins or cotters, etc. The output and supply conductors 15 of amplifier 11 can be made accessible from outside the shaft 50 through a bore 51 made for example as illustrated.

In FIG. 10 it is illustrated a further example of embodiment of a sensor S according to the invention onto a mechanical piece W, for sensing in particular torsional and flexural stresses. The piece W has a cylindrical shape, with an intermediate portion 60 having a smaller diameter. Onto the surface of a facet or notch 61 of said intermediate portion there is applied a sensor S according to the invention.

The sensor according to the invention can be attached to mechanical members or structures by means of glues or cements, but also in other ways, for example in the way shown in FIG. 7: the sensor is applied onto the surface of a member W and is blocked against said member by means of clamping plates 20 and 30 which are fixed to the member W by means of screws 25 screwed in corresponding threaded holes made in member W. Conveniently, the plates 20 and 30 on their respective surface facing the member W have respective recesses adapted to receive corresponding end portions of the substrate of the sensor.

Whatever the way of connecting the sensor according to the invention to a member or structure for sensing stresses or deformations may be, the signal which it makes available has a level by far higher than the signal level available with the use of conventional strain gauges.

The sensor according to the invention can be conveniently used in quite different situations, and in particular for sensing stresses and deformations in shafts, pivots, axles, leverages, support structures, suspensions, shock absorbers, leaf springs, etc. It can also be used for sensing stresses and deformations in reservoirs, pipings and tubings, etc., as well as for sensing vibrations, deformations and stresses in slabs, in particular of glass, crystal and the like. The sensor can also be used as vibration detector in antitheft devices.

The sensor can be also conveniently used for detecting stresses and deformations in walls, columns, floors, etc., as well as in weighing apparatus.

Naturally, the invention covers all those embodiments which allow achieving the same useful results by means of the same inventive idea.

We claim:

1. A strain gauge sensor for sensing stress and deformations in a mechanical member, said sensor comprising a support substrate in the form of a thin rectangular plate separate from said member but adapted to be secured to said member, said plate being made of an electrically insulating ceramic material, said plate having an upper surface and a lower surface, a plurality of thick-film resistors deposited on said upper surface and surface metal tracks on said upper surface connected to said thick-film resistors for connecting said resistors to circuits remote from said plate, said lower surface of said support substrate being adapted to be firmly attached onto said member of which stresses and deformations are to be locally sensed so that said stresses and deformation of said member cause, through the substrate, corresponding deformations of said thick-film resistors and clamping means for clamping the sensor to said mechanical member, said clamping means comprising a pair of plates each having recess in one surface adapted to overlie and engage opposite ends of said substrate with each end of said substrate being located within a respective recess and means for securing said plates to said mechanical member.

* * * * *